United States Patent

Mäusli

[11] Patent Number: 5,846,817
[45] Date of Patent: Dec. 8, 1998

[54] BIOREACTOR, IN PARTICULAR FOR MICROGRAVITY

[75] Inventor: Pierre-Alain Mäusli, Cheseaux, Switzerland

[73] Assignee: Agence Spatiale Europeenne, Paris Cedex, France

[21] Appl. No.: 520,578

[22] Filed: Aug. 29, 1995

[30] Foreign Application Priority Data

Sep. 2, 1994 [FR] France .................................. 94 10567

[51] Int. Cl.$^6$ .................................................. C12M 1/06
[52] U.S. Cl. .................................. 435/293.1; 435/293.2; 435/286.7; 435/297.1; 435/297.3; 261/81; 261/122.1
[58] Field of Search .............................. 435/286.7, 289.1, 435/293.1, 293.2, 297.1, 297.2, 297.3, 302.1, 813, 819; 261/81, 82, 122.1; 366/102, 103, 105, 262, 276, 277, 289, 303, 307, 315, 317; 417/338, 339, 340; 418/55.1, 55.4

[56] References Cited

U.S. PATENT DOCUMENTS

| | | | |
|---|---|---|---|
| 2,667,407 | 1/1954 | Fenske et al. | 261/81 |
| 3,855,368 | 12/1974 | Prochazka et al. | 261/81 |
| 4,756,675 | 7/1988 | Kakuda et al. | 418/55 |
| 4,911,621 | 3/1990 | McCullough | 418/55 |
| 5,002,890 | 3/1991 | Morrison . | |

FOREIGN PATENT DOCUMENTS

| | | | |
|---|---|---|---|
| 317811 | 5/1989 | European Pat. Off. . | |
| 362408 | 4/1990 | European Pat. Off. . | |
| 160155 | 5/1983 | Germany | 435/297.3 |
| 1696472 | 12/1991 | U.S.S.R. | 435/305.1 |
| 1145561 | 3/1969 | United Kingdom . | |
| WO 89/09814 | 10/1989 | WIPO . | |

*Primary Examiner*—William H. Beisner
*Attorney, Agent, or Firm*—Bell Seltzer Intellectual Property Law Group; Alston & Bird LLP

[57] ABSTRACT

A bioreactor, in particular for a microgravity, comprising at least one cell culture chamber, an oxygen supply and an agitator for a cell culture. In particular, the chamber includes two housing elements (1, 2) having a first (1', 9) and a second (2', 9') wall region, as well as a first (3) and a second (4) separating element extending from respectively the first (1', 9) and the second (2', 9') wall regions in the direction respectively of the second (2', 9') and the first (1', 9) wall regions. The separating region or regions of the separating elements has (have) a height (h) less than the distance (D) between the first (1', 9) and the second (2', 9') wall regions. The agitator includes a first and second devices (7) for moving the two housing elements (1, 2) with respect to each other.

10 Claims, 6 Drawing Sheets

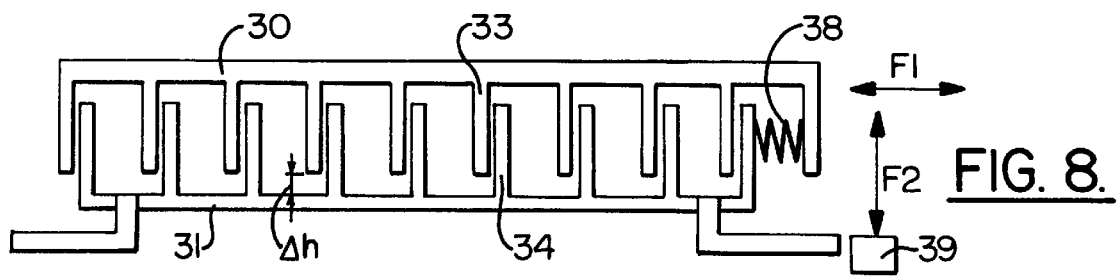
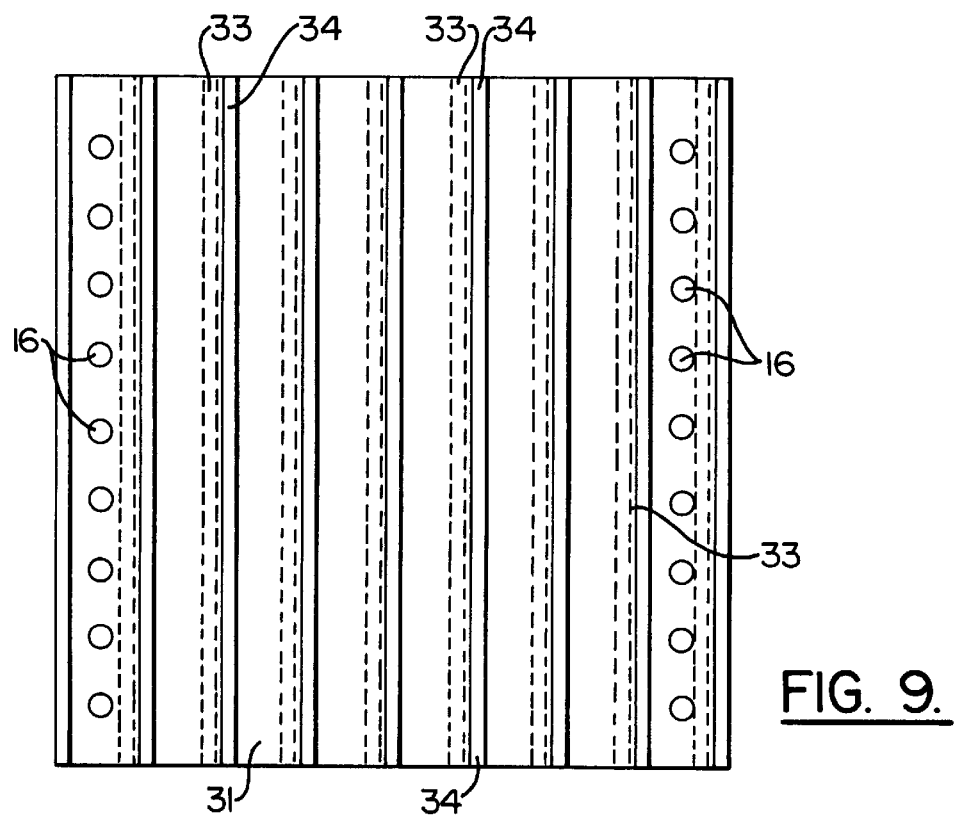

BIOREACTOR, IN PARTICULAR FOR MICROGRAVITY

BACKGROUND OF THE INVENTION

The subject of the present invention is a bioreactor, in particular for a microgravity, comprising at least one cell culture chamber, a means for supplying oxygen to the said chamber and a means for agitating the cell culture enabling the latter to come into contact with the oxygen supplied to the chamber.

Under the microgravity conditions such as encountered in satellites, it is particularly desirable that the agitation of the cell culture liquid be as small as possible. Moreover, bioreactors usable under microgravity conditions impose constructional principles which are different from those intended solely for terrestrial applications because of the fact that, under microgravity conditions, convection phenomena do not exist. Another constraint is the need for good aeration and good homogeneity of the cell culture liquid, coupled with as automatic an operation as possible, especially for cleaning.

The subject of the U.S. Pat. No. 5,002,890, granted to the American State on 26 Mar. 1991, is a bioreactor which can be used under microgravity conditions and which includes a vertical chamber in which a set of rotary filters arranged in a central position interact with flexible membranes which are arranged so as to rotate annularly about the set of filters. In this bioreactor, the agitation and mixing process relies on the dynamics of the fluids and consequently depends to a large extent on the speed of rotation. Such a bioreactor therefore does not allow a low rotation speed.

The subject of the present invention is a bioreactor making it possible to avoid at least the aforementioned drawback.

SUMMARY OF THE INVENTION

The bioreactor according to the invention is, for this purpose, characterized in that the cell culture chamber includes a first and a second housing element having respectively a first and a second wall region which face each other, as well as a first and a second separating element comprising at least a first and a second separating region extending from respectively the first and the second wall regions in the direction respectively of the second and the first wall regions, in that the separating region or regions of at least one of the separating elements has (have) a height less than the distance between the first and the second wall regions, and in that the agitation means includes a means for moving the first and the second housing elements with respect to each other, thereby allowing the distance between the separating elements and/or the housing elements to be varied.

A bioreactor as defined hereinabove allows oxygenation of the cell culture liquid with a very low level of agitation and without significant acceleration of the microorganisms, while at the same time allowing sufficient homogeneity of the culture.

The first and the second separating regions advantageously have a height less than the distance between the first and the second wall regions. This allows even better oxygenation of the cell culture liquid.

The first and the second wall regions may be plane.

The first and the second wall regions may be parallel.

At least one separating region may be plane.

According to a preferred embodiment, the first and the second separating elements have a first and a second spiralled separating region, which may advantageously exhibit substantially identical growth laws.

The means for moving the first and the second housing elements with respect to each other may then include a device for putting the first and the second housing elements into alternating rotation with respect to each other. The bioreactor may also include a device for moving the first and the second housing elements translationally with respect to each other so as to vary the distance between the said housing elements. The bioreactor may include a means for putting an inlet and an outlet of the chamber into communication, something which furthermore achieves circulation of liquid by a pumping effect obtained by the alternating operation of the translational device.

The rotational device and the translational device may be operated simultaneously.

The bioreactor may include a means for putting the two spirals into abutment against each other, by relative rotation of the first and the second housing elements, so that the chamber is in the form of a continuous tube.

At least one wall region may be porous to the gases, at least over part of its surface, and the means for supplying oxygen to the chamber may then include a means for blowing in oxygen through a said porous wall region.

According to another embodiment, the first and the second wall regions are cylindrical. The first and the second wall regions may, for example, be coaxial. The means for moving the first and the second housing elements with respect to each other may then include at least one device for moving the first and the second cylindrical wall regions in relative translation.

At least one separating region may advantageously include at least one cylindrical tray.

BRIEF DESCRIPTION OF THE DRAWINGS

Other characteristics and advantages of the invention will be more apparent on reading the following description, given by way of non-limiting example, in conjunction with the drawings in which:

FIGS. 8 and 9 represent a diagrammatic view respectively in vertical section and in plan view of a bioreactor according to a second embodiment of the invention.

DETAILED DESCRIPTION OF THE PREFERRED EMBODIMENTS

Figure 1:
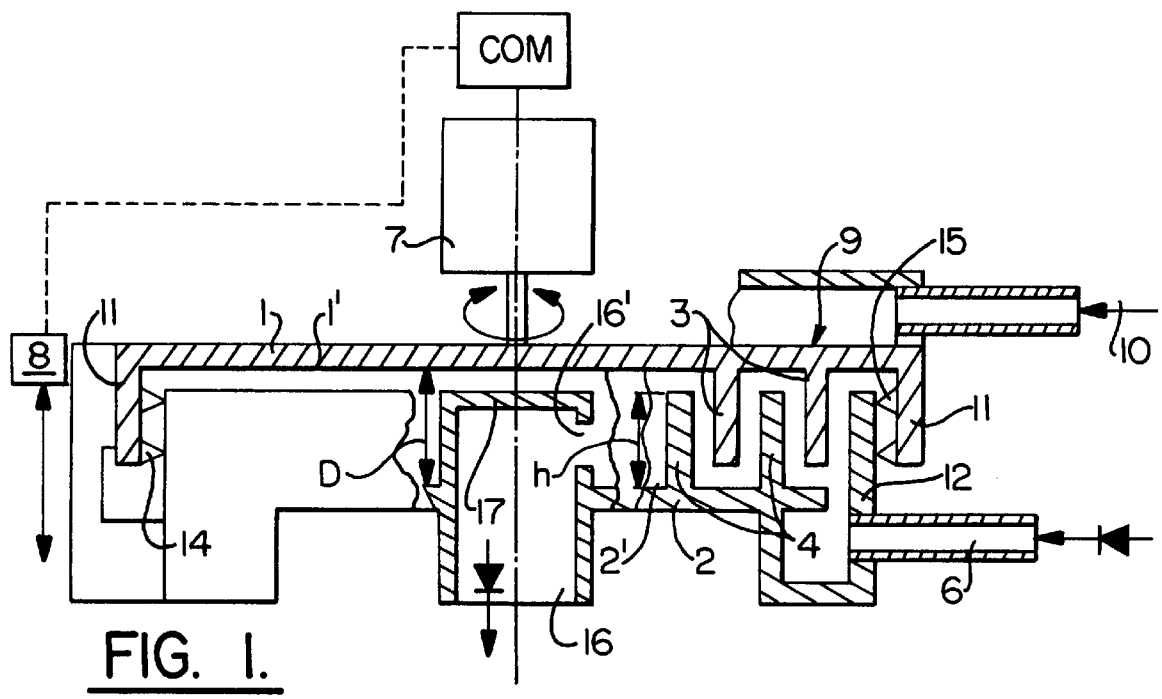
FIGS. 1 and 2 represent a diagrammatic view of a bioreactor according to the invention, respectively in vertical section and in plan view.
Figure 2:
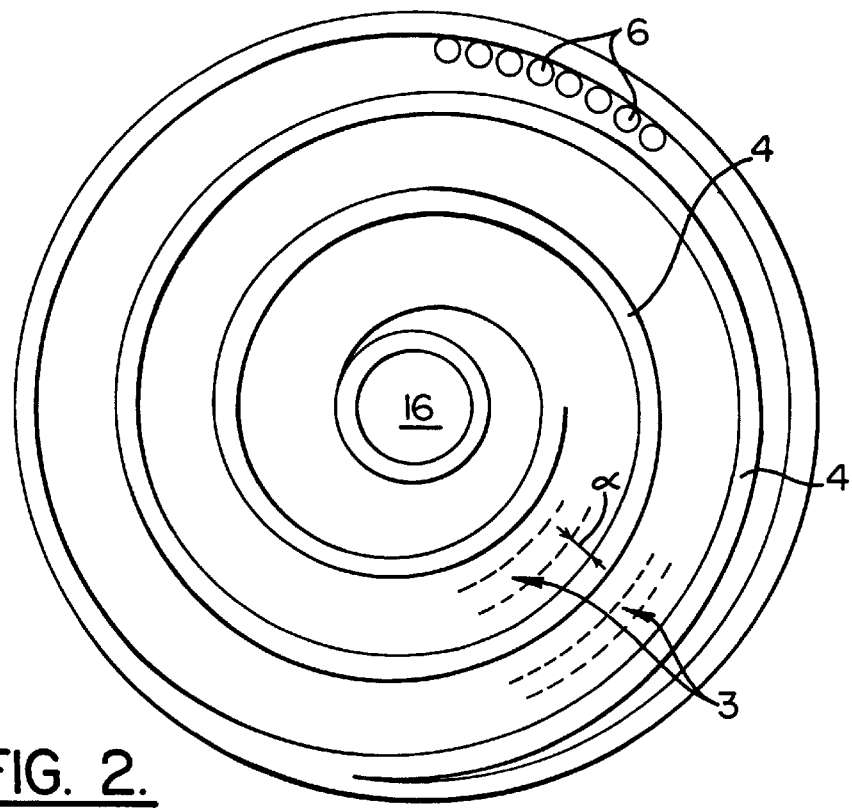

As shown in FIGS. 1 and 2, a bioreactor according to the invention includes an active volume delimited by two complementary flat housings 1 and 2, each of which has a wall region, respectively 3 and 4, extending from an outer wall, respectively 11 and 12, as far as a central region 16, 17. The inlet of the cell culture liquid is distributed over the perimeter of the external wall 12 which has, for this purpose, a plurality of pipelines 6. The central region is delimited by an upper edge 17 and is provided with an opening 16, 16' for outlet of the liquid. Inlet and outlet one-way valves, not shown, may be employed.

The two flat housings 1 and 2 are mounted with respect to each other so that their spiralled wall regions (or walls) 3 and 4 interpenetrate so as to create a large wall surface which is distributed homogeneously over the internal volume of the reactor between the housings 1 and 2 in order to form a cell culture chamber. The height h of one and/or both of the spiralled walls 3 and 4 is such that it is less than the nominal distance $D_0$ between the internal walls 1' and 2' of the housings 1 and 2. A motor 7 drives the housing 1 in alternating rotation about a spindle shown conventionally as being vertical and a device 8 enables the distance D between the two housings 1 and 2 to be varied with respect to the nominal distance $D_0$ by translation.

The bioreactor as described hereinabove can operate in three modes:

In the first mode, once the cell culture chamber has been filled, the inlets 6 and the outlet 16 are closed off and mixing is achieved by virtue of the alternating rotational movement generated by the motor 7. This movement does not change the total volume of the reactor but, locally, the horizontal distance between the spiralled walls 3 and 4 is modified, thereby forcing the cell culture liquid to move around the said walls. Given that the entire volume is affected equally by this movement, mixing is homogeneous and its amplitude can be regulated by varying the speed of the motor 7 and the amplitude of the alternating rotation. It is also possible to choose the distance $\Delta h$ between the walls 3 and 4 and the inner edges, respectively 1' and 2'.

According to the second operating mode, a pumping action is obtained using the translational drive device 8. In this configuration, the inlets 6 and the outlet 16 are open, that is to say the aforementioned one-way valves are passing fluid. Mixing is now the result of a combination of the two, rotational and translational, movements.

The third operating mode is obtained by rotating the housings 1 and 2 with respect to each other using the motor 7 until the walls 3 and 4 come into contact with each other. A long spiralled tube is thus obtained and fluid movement may be obtained by alternating driving of the translational device 8.

As a result of the above, the agitation of the liquid suspension forming the cell culture is obtained by the relative movements of the two spiralled walls or wall regions 3 and 4. These movements, whether they are rotational or translational, generate vortices locally, which are distributed homogeneously over the volume of the bioreactor. The local acceleration depends on the relative speed of the two housings 1 and 2 as well as on the distance $\Delta h$ separating the top of one spiralled wall of one housing from the inner edge of the other housing. As a result, the acceleration can thus be regulated continuously from the 0 value.

In the first mode described hereinabove, the mixing may lead to a flow and a counterflow without long-range mixing occurring. This drawback may be overcome by interconnecting the outlet valves and to the inlet so as to loop the chamber back on itself. In the case where a flow is generated, the mixing range is especially increased.

Gas exchange may be achieved by means of a porous wall region mounted at the upper part of the housing 1 and gas containing oxygen is introduced through this porous wall region by means of a gas inlet 10. The gas exchange surface may preferably be such that it provides as short a distance as possible of the gas inlet from each point in the liquid. By means of the mixing method described hereinabove and the particular geometry described, the liquid is periodically close to the internal walls 1' and 2' of the housings 1 and 2, this being favourable to gas exchange.

Elements 9 are preferably distributed over the entire upper surface of the housing 1. They may be made of a liquid-impermeable porous material or of a gas-permeable membrane. It is possible, for example, to use ceramics, expanded PTFE such as that sold under the GORETEX trade mark, or alternatively silicone. The criteria for choosing the placements are accessibility for maintenance, homogeneity of the gas exchange, biocompatibility, mechanical strength and the possibility of obtaining sterilization.

Figure 3:
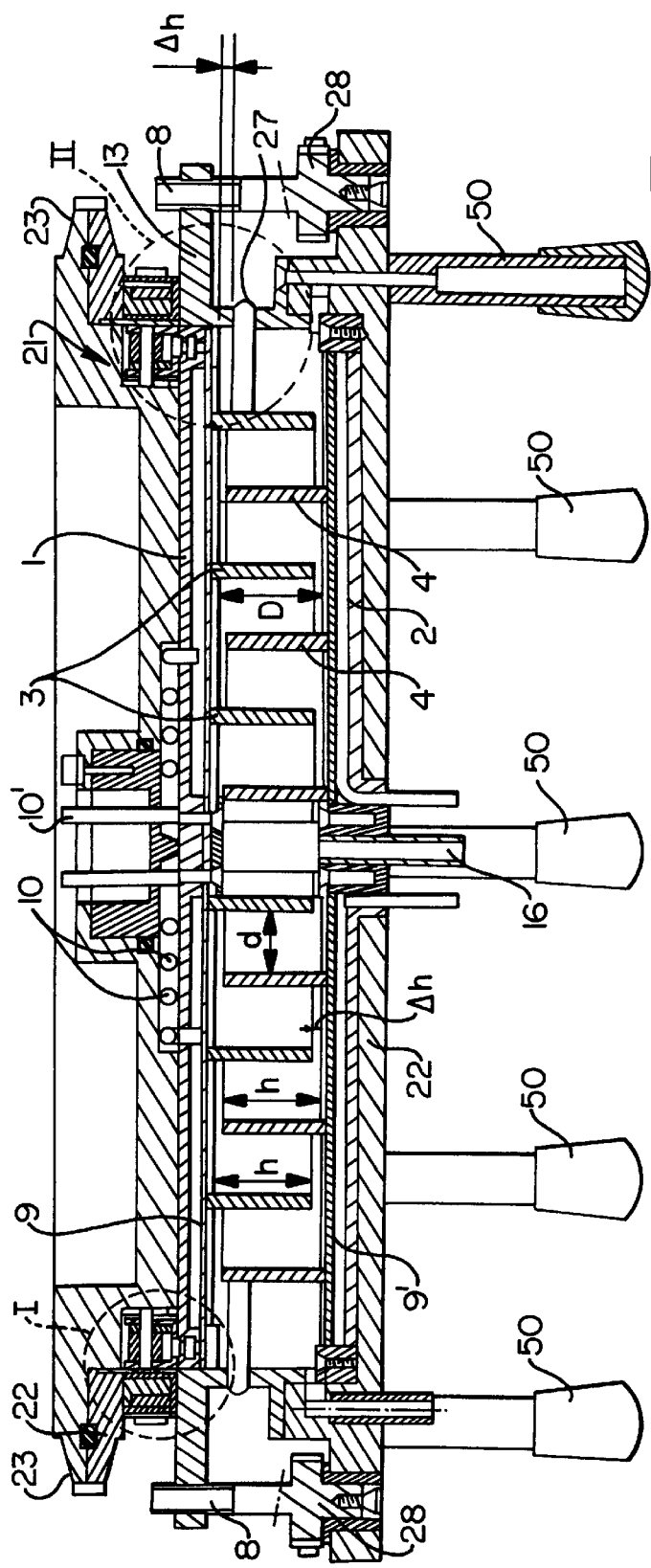
FIG. 3 represents a vertical section of a bioreactor according to a preferred embodiment of the invention.

Oxygenation and $CO_2$ removal, which need to be carried out while avoiding any creation of microgravity bubbles, may be achieved as shown in FIG. 3 by using exchange membranes or porous walls 9, 9'. Given that the diffusion length is very short in the liquid, this dictates that the exchange surface area be very large and be distributed homogeneously over the volume or else that the entire volume of the liquid be forced periodically to be in the immediate vicinity of the exchange surface. This latter condition is easily achieved using the concept of the bioreactor described hereinabove, given that the entire volume of the liquid is induced to pass through the regulatable gap $\Delta h$ during the rotational movement of the spiral 34.

Referring now to FIG. 3, the housings 1 and 2 delimiting the active volume of the chamber of the reactor are placed in a rigid support which includes a cover 21 and a base in two parts 22 and 13, the part 13 being connected to the part 12 via an elastic membrane 27 which allows translational movement suitable for regulating the gap $\Delta h$.

Figure 6:
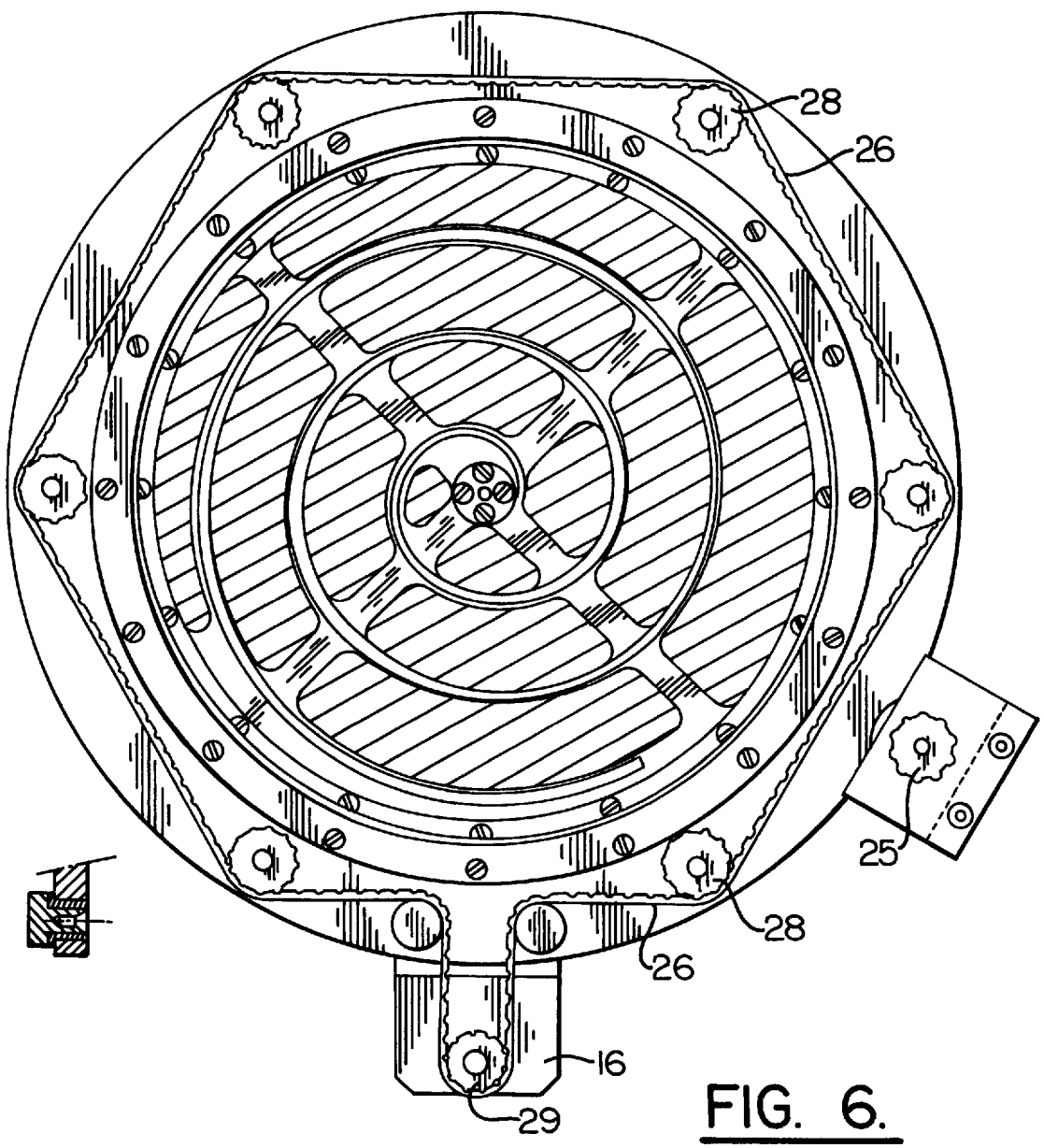
FIG. 6 represents a horizontal section, seen from above, of the lower housing of the bioreactor of FIG. 3.

This translational movement may be performed, for example as shown in FIG. 6, by an external driving device 16 having a drive wheel 9 controlling a chain 26 which rotates toothed wheels 28 having a threaded extension 8 engaging in tapped parts of the piece 13, which piece 13 carries the cover 21 and the housing 1 as well as the membrane 9.

Figure 5:
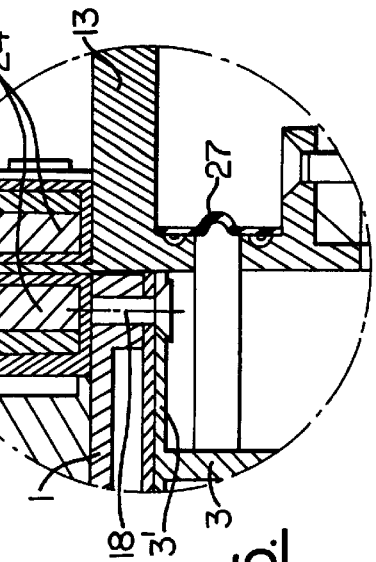
FIG. 5 being an enlarged view of that part of FIG. 3 circled at II.
Figure 4:
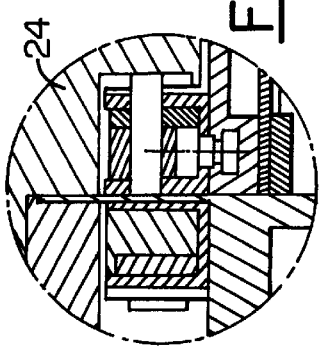
FIG. 4 being an enlarged view of that part of FIG. 3 circled at I.
Figure 7:
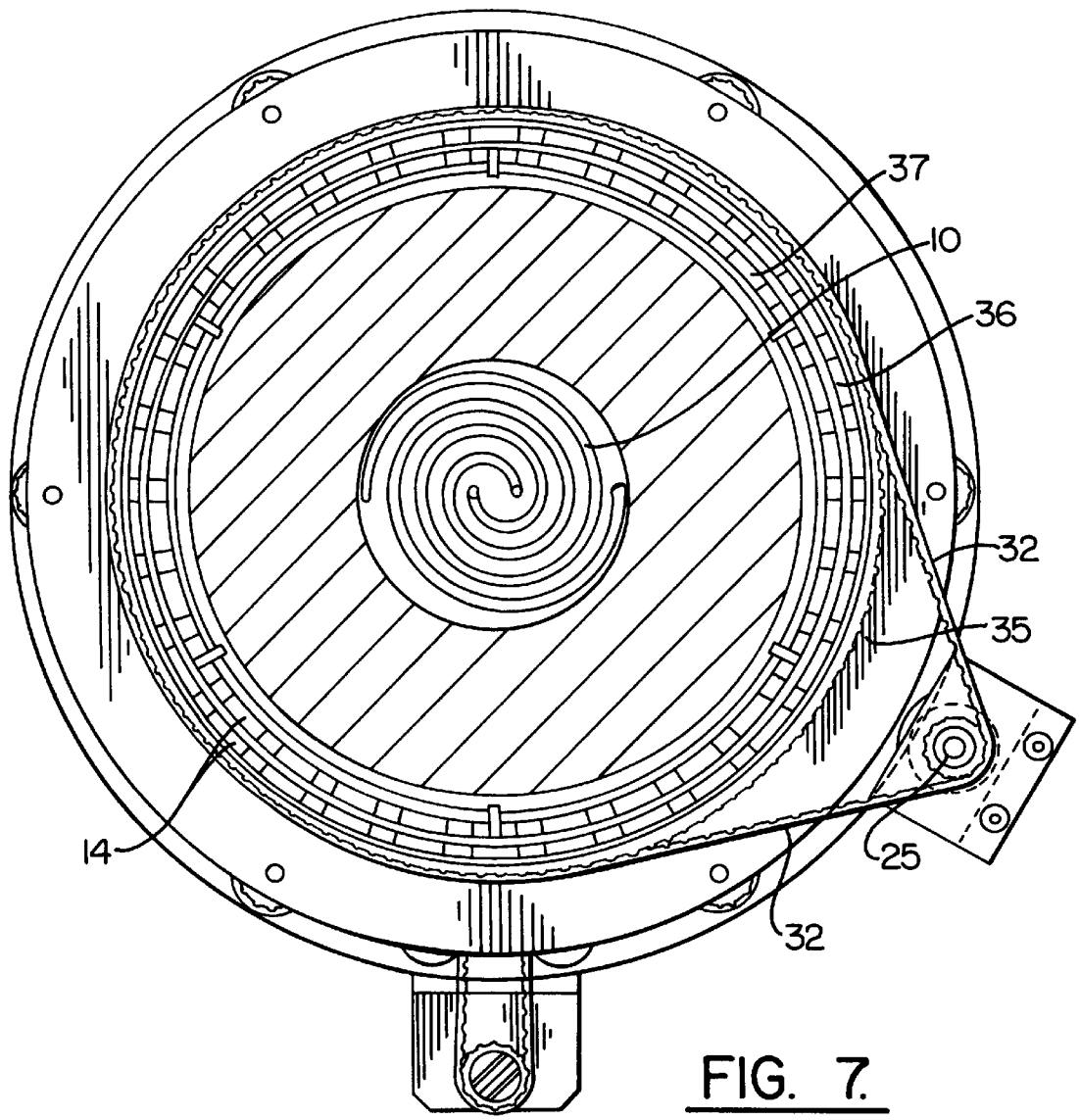
FIG. 7 is a view from above, in partial section, of the upper housing of the bioreactor of FIG. 3.

The parts of the bioreactor which are put into rotation are the elements 1, 3 and 9. They are driven (see FIGS. 4, 5 and 7) by a magnetic device having magnets 14, a first series of magnets being distributed around the perimeter of a ring 36 rotationally driven by a motor 25 with toothed wheels driving a chain 32 rotating a crown gear 35 carried by the periphery of the ring 36. A second series of magnets 14 is carried by a ring 37 internal to the housing 1, which is integral with the latter. FIG. 7 also shows the circulation of air (or oxygen) which may be carried out by means of piping 10 which is arranged in a spiral, this arrangement eliminating the need for rotary seals.

The materials used for implementing the bioreactor are biocompatible and stovable so that each element, whether assembled or not, is sterilizable.

The spiralled structure allows easy assembly and disassembly, as well as cleaning without great difficulty.

In the embodiments shown in FIGS. 8 and 9, the upper and lower housings, respectively 30 and 31, have a rectangular or square shape and each comprise a plurality of parallel longitudinal walls, respectively 33 and 34.

Agitation of the liquid may be obtained by translational movement in two orthogonal directions along the direction of arrow F1 (device 38) in order to vary the distance between the walls 33 and 34 and/or the arrow F2 (device 39) in order to vary the gap Δh. The liquid inlets are referenced 6' and the liquid outlets are referenced 16'.

Figure 10:
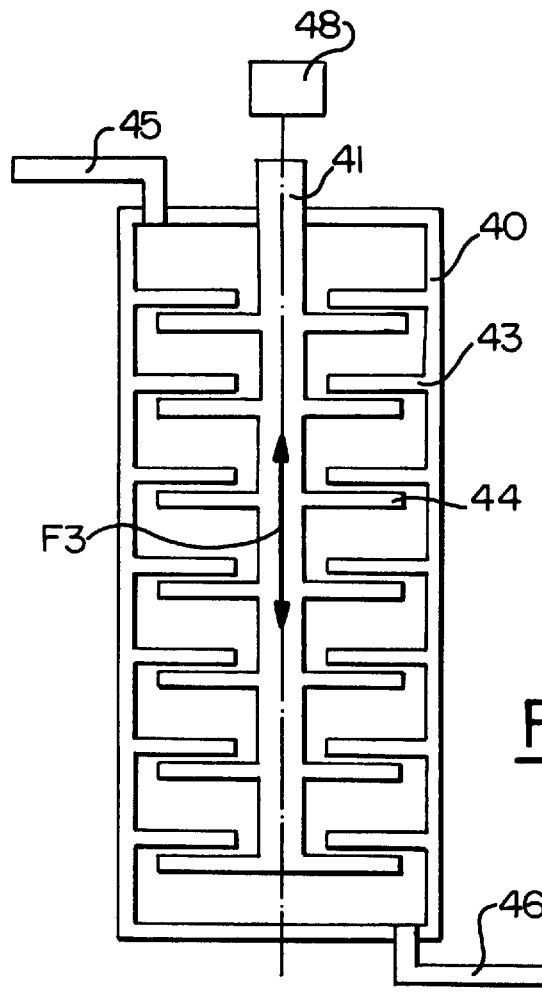
FIGS. 10 and 11 represent respectively in vertical section and in plan view a third embodiment of the invention.
Figure 11:
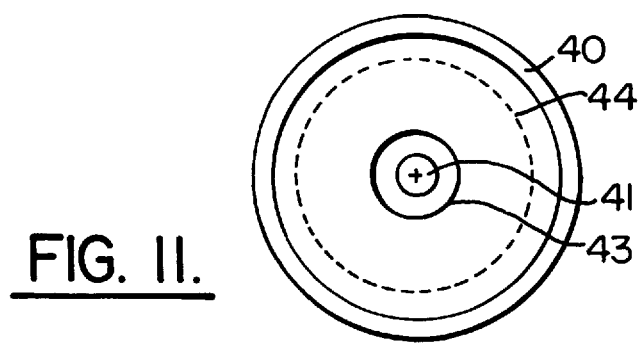

The embodiment of FIGS. 10 and 11 employs a concentric structure in which the active volume of the reactor is defined by the external cylindrical parts 40 seen from annular wall regions 33, these being imbricated with annular wall regions 44 carried by a cylinder or a central piston 41. The distance between the annular walls 43 and 44 may be modified, by means of the motor 48, in the direction of the arrow F3. The liquid supply takes place at the top via the pipe 45 and discharge at the bottom via the discharge pipe 46.

I claim:

1. Bioreactor for use under microgravity conditions comprising:
   at least one cell culture chamber,
   an oxygen supply for at least one chamber; and
   an agitator for agitating a cell culture so as to enable contact with oxygen supplied to said chamber, said chamber comprises:
   (i) a first and a second housing element having respectively a first and a second wall region which face each other, with said first and second having elements being separated by a distance (D);
   (ii) a first separating element comprising at least one first separating region extending from the first wall region towards the second wall region;
   (iii) a second separating element comprising at least one second separating region extending from the second wall region towards the first wall region, wherein the first and second separating elements are separated by a distance (d) and the separating region or regions of at least one of the separating elements have a height (h) less than the distance (D), and said agitator comprises (i) a first device displacing the first and the second housing elements with respect to each other so as to vary the distance (d) between the first and second separating elements, and (ii) a second device for displacing the first and the second housing elements with respect to each other so as to vary the distance (D) between said first and second housing elements.

2. The bioreactor according to claim 1 wherein at least one of the first and second wall regions are planar.

3. The bioreactor according to claim 1 wherein the first device of the agitator provides for rotary agitation of the first and second housing elements.

4. Bioreactor according to claim 1, wherein at least one wall region is porous to the gases, at least over part of its surface, and wherein the means for supplying oxygen to the chamber includes a means for blowing in oxygen through a said porous wall region.

5. Bioreactor for use under microgravity conditions comprising:
   at least one cell culture chamber,
   an oxygen supply for at least one chamber; and
   an agitator for agitating a cell culture so as to enable contact with oxygen supplied to said chamber, said chamber comprises:
   (i) a first and a second housing element having respectively a first and a second wall region which face each other, with said first and second having elements being separated by a distance (D);
   (ii) a first separating element comprising at least one first separating region extending from the first wall region towards the second wall region;
   (iii) a second separating element comprising at least one second separating region extending from the second wall region towards the first wall region, wherein the first and second separating elements are separated by a distance (d) and the separating region or regions of at least one of the separating elements have a height (h) less than the distance (D), and said agitator comprises a device for displacing the first and the second housing elements with respect to each other so as to vary the distance (D) between said first and second housing elements, wherein the first and second separating regions are spiralled separating regions.

6. Bioreactor according to claim 5, wherein the spirals of the first and of the second spiralled separating regions exhibit substantially identical growth laws.

7. Bioreactor according to claim 5, wherein said means for moving the first and the second housing elements with respect to each other includes a device for putting the first and the second housing elements into alternating rotation with respect to each other so as to vary the distance (d) between the separating elements.

8. Bioreactor according to claim 7, including a means for putting an inlet and an outlet of the chamber into communication.

9. Bioreactor according to claim 8, including a control means for simultaneously actuating the rotational device and the translational device.

10. Bioreactor according to claim 5, including a means for putting the two spiralled separating regions into abutment against each other, by relative rotation of the first and the second housing elements, so that the chamber is in the form of a continuous tube.

* * * * *